US011045668B2

(12) United States Patent
Roa et al.

(10) Patent No.: US 11,045,668 B2
(45) Date of Patent: Jun. 29, 2021

(54) THREE-DIMENSIONAL DETECTOR FOR RADIOTHERAPY VERIFICATION

(71) Applicant: HRS International Solutions, LLC, Henderson, NV (US)

(72) Inventors: Dante E. Roa, Mission Viejo, CA (US); Jimmy Hernandez Bello, Waunakee, WI (US); Jose Vidal Valladolid Salazar, Rimac (PE); Roger Challco Chalco, Rimac (PE); Carmen Sandra Guzman Calcina, Rimac (PE); Modesto Edilberto Montoya Zavaleta, Rimac (PE); Andres Miguel Gonzales Galvez, San Isidro (PE)

(73) Assignee: HRS International Solutions, LLC, Henderson, NV (US)

(*) Notice: Subject to any disclaimer, the term of this patent is extended or adjusted under 35 U.S.C. 154(b) by 70 days.

(21) Appl. No.: 16/672,910

(22) Filed: Nov. 4, 2019

(65) Prior Publication Data
US 2020/0139157 A1 May 7, 2020

Related U.S. Application Data

(60) Provisional application No. 62/755,322, filed on Nov. 2, 2018.

(51) Int. Cl.
*A61N 5/10* (2006.01)

(52) U.S. Cl.
CPC ........ *A61N 5/1071* (2013.01); *A61N 5/1077* (2013.01); *A61N 2005/1092* (2013.01)

(58) Field of Classification Search
CPC combination set(s) only.
See application file for complete search history.

(56) References Cited

U.S. PATENT DOCUMENTS

| 7,872,750 B1* | 1/2011 | Wrbanek | G01N 15/02 356/336 |
|---|---|---|---|
| 8,044,359 B2 | 10/2011 | Simon | |
| 2003/0231740 A1* | 12/2003 | Paliwal | A61N 5/1048 378/167 |
| 2016/0048981 A1* | 2/2016 | Pearlstein | G06T 15/08 382/128 |
| 2019/0175950 A1* | 6/2019 | Nagumo | G01T 1/2023 |

* cited by examiner

*Primary Examiner* — Hoon K Song
(74) *Attorney, Agent, or Firm* — Boyle Fredrickson, S.C.

(57) ABSTRACT

A volumetric radiation dose detector provides radiation sensors distributed along a closed surface presenting surface normals that vary over a range of azimuth and altitude angles to provide accurate dose modeling for radiation received at a comparable range of angles. Concentric layers of surfaces provide volumetric dose information that can be used to directly produce useful dose maps and assessments.

17 Claims, 5 Drawing Sheets

THREE-DIMENSIONAL DETECTOR FOR RADIOTHERAPY VERIFICATION

CROSS REFERENCE TO RELATED APPLICATION

The present application claims the benefit of U.S. provisional application 62/755,322 filed Nov. 2, 2018, and hereby incorporated by reference.

STATEMENT REGARDING FEDERALLY SPONSORED RESEARCH OR DEVELOPMENT

. . .

BACKGROUND OF THE INVENTION

The present invention relates generally to radiation therapy equipment and in particular to a dosimeter for quality assessment of radiotherapy equipment and patient specific quality assurance (QA) plans.

Nearly 200,000 patients are diagnosed with brain metastases in the United States alone and many of them could benefit from intracranial stereotactic radiosurgery (SRS) treatments. SRS is a radiotherapy treatment that delivers an ablative dose of radiation (16-24 Gy) in one treatment session to one or more brain metastases with submillimeter precision and with greater dose conformity than conventional radiotherapy. Advances in linear accelerator (linac) technology have made SRS accessible to more patients and, in recent years, has transformed intracranial SRS into a routine treatment modality.

Verification and quality assurance of SRS dose delivery prior to patient treatment is of great importance since an error could reduce the effectiveness of the high-resolution treatment. Current dose verification systems include radiochromic film, thermoluminescent dosimeters (TLD), and gel-based dosimeters which provide accurate measured dose information in two- and three-dimensional formats. However, these systems can require a day or more for calibration and data processing prior to getting results, which is impractical and costly in a busy clinic.

Commercially available electronic detector arrays can provide dosimetric results in minutes but have low resolution and two-dimensional form factors which require time-consuming repositioning or mathematical techniques to deduce three-dimensional data. Low sampling resolution and a two-dimensional form factor can lead to inaccuracies when multiple dose regions over a range of angles are compressed into two dimensions.

SUMMARY OF THE INVENTION

The present invention provides a dose verification instrument that can make direct and accurate high-resolution dose measurements at arbitrary beam angles. The detectors are arrayed on surfaces that curve in two dimensions (for example, a sphere) to permit measurements of beams at arbitrary angles applicable to intracranial stereotactic radiosurgery and similar techniques. The detectors can also be arrayed within a volume defined by the surface for a direct three-dimensional dose readout.

More specifically, in one embodiment, the invention provides a radiotherapy dose verification instrument having a radiolucent support structure and a plurality of first solid-state electronic radiation detectors held by the radiolucent support structure at separated locations defining an outer closed surface enclosing a volume of the radiolucent support structure. A plurality of second solid-state electronic radiation detectors are dispersed within the volume. Each of the first and second plurality of solid-state electronic radiation detectors are attached to conductors receiving electronic signals from the solid-state electronic radiation detectors indicating radiation dose at each of the first and second plurality of solid-state electronic radiation detectors for output. The closed surface presents surface normals at the solid-state electronic radiation detectors distributed at multiple angles in each of two perpendicular planes.

It is thus a feature of at least one embodiment of the invention to provide a verification instrument that can provide direct volumetric dose measurements mimicking those of tissue for a variety of beam angles to provide flexibility in verification of SRS treatment plans.

More than 90% of the volume may be occupied by a water equivalent material.

It is thus a feature of at least one embodiment of the invention to allow the dose verification instrument to accurately simulate attenuation and scatter to eliminate or reduce the need for complex scatter calculations and attenuation.

The first plurality of solid-state electronic radiation detectors may be substantially uniformly distributed over the outer closed surface, and the second plurality of solid-state electronic radiation detectors may be substantially uniformly distributed within the volume.

It is another feature of at least one embodiment of the invention to provide both surface and internal sensors to permit direct reading of dose distributions for reduced measurement ambiguity and high-speed dose reconstruction.

The second plurality of solid-state electronic radiation detectors may define a set of corresponding nested closed surfaces concentric within the outer closed surface, and the second plurality of solid-state electronic radiation detectors are substantially uniformly distributed over corresponding nested closed surfaces.

It is thus a feature of at least one embodiment of the invention to define a sensor layout well adapted for common isocentric treatment plans.

The volume of the radiolucent support structure may be constructed of a set of inter-fitting shells each having an outer surface defining at least one of the outer closed surface or corresponding nested closed surface, the shells adapted to be individually fabricated and the solid-state electronic radiation detectors to be attached to at least one exposed surface of each shell.

It is thus a feature of at least one embodiment of the invention to provide a method of fabrication allowing high-density, accurate detector placement within a volume.

The detectors may be positioned to measure entrance and exit doses of radiation passing along a straight line through the volume.

It is thus a feature of at least one embodiment of the invention to allow entrance and exit doses to be determined for improved accuracy and reduction in ambiguity from crossing beams, and to permit accurate assessment of beam trajectory for calibration purposes.

The radiation detectors may be integrating detectors of radiation intensity.

It is thus a feature of at least one embodiment of the invention to provide a method of direct dose determination insensitive to sampling rates which may be reduced with extremely high numbers of detectors needed for high-resolution.

The radiotherapy dose verification instrument may include a calibration circuit receiving the electronic signals and operating to:

(1) determine a trajectory of a radiation beam striking the radiolucent support structure and only a subset of the plurality of solid-state electronic radiation detectors; and (2) correct the electronic signals for angular sensitivity variations of the subset of the plurality of solid-state electronic radiation detectors based on the deduced trajectory.

It is thus a feature of at least one embodiment of the invention to provide a detector that can accommodate beams at a variety of angles while managing angle sensitivity of the individual detectors.

The outer closed surface may be a sphere.

It is thus a feature of at least one embodiment of the invention to provide a volume shape adaptable not only for the brain but other anatomies.

The radiotherapy dose verification instrument may further include an electronic computer executing a stored program held in non-transitory memory and operating to receive the electronic signals to provide an output selected from the group consisting of a conformity index, a gradient index, a dose volume histogram, and a 3D percent dose difference per distance to agreement.

It is thus a feature of at least one embodiment of the invention to provide the data necessary for direct calculation of a wide range of recognized and useful measurements of treatment dose.

These particular objects and advantages may apply to only some embodiments falling within the claims and thus do not define the scope of the invention.

DETAILED DESCRIPTION OF THE PREFERRED EMBODIMENT

Figure 1:
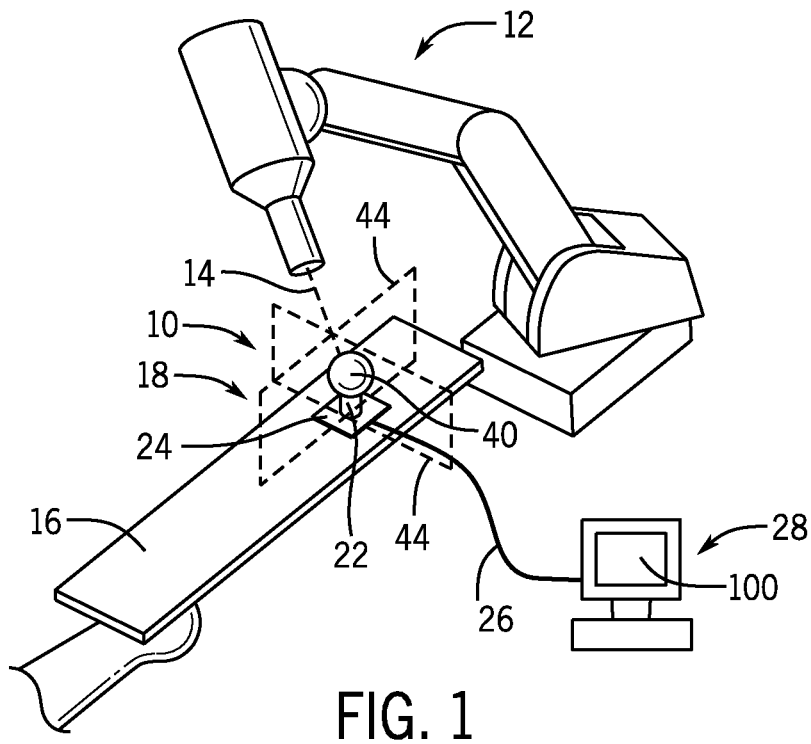
FIG. 1 is a simplified perspective diagram of a radiotherapy machine capable of maneuvering in multiple dimensions about a patient table and showing a dose verification instrument according to one embodiment of the present invention positioned for quality assurance of the radiation machine.

Referring now to FIG. 1, a radiation detector system 10 of the present invention may be used with radiotherapy equipment 12 of a type providing a radiation beam 14 that may be directed toward a patient table 16 at a variety of angles distributed in both azimuth and altitude about a treatment region 18. The detector system 10 may be located with respect to a known fiducial of the radiotherapy equipment 12 (not shown) to position measurement volume 20 centered around the treatment region 18.

In one embodiment, the measurement volume 20 may be supported, for example, on an upwardly extending cylindrical column 22 which in turn extends from a horizontal plane or base 24 supported on the patient table 16. The detector system 10 may communicate via electrical cable 26 or wirelessly to a computer 28 that may receive electrical signals from the detector system 10 indicating radiation dose at a variety of locations within the measurement volume 20. Using that data the computer 28 may provide for the display of dose information in a variety of forms as will be discussed below.

Figure 2:
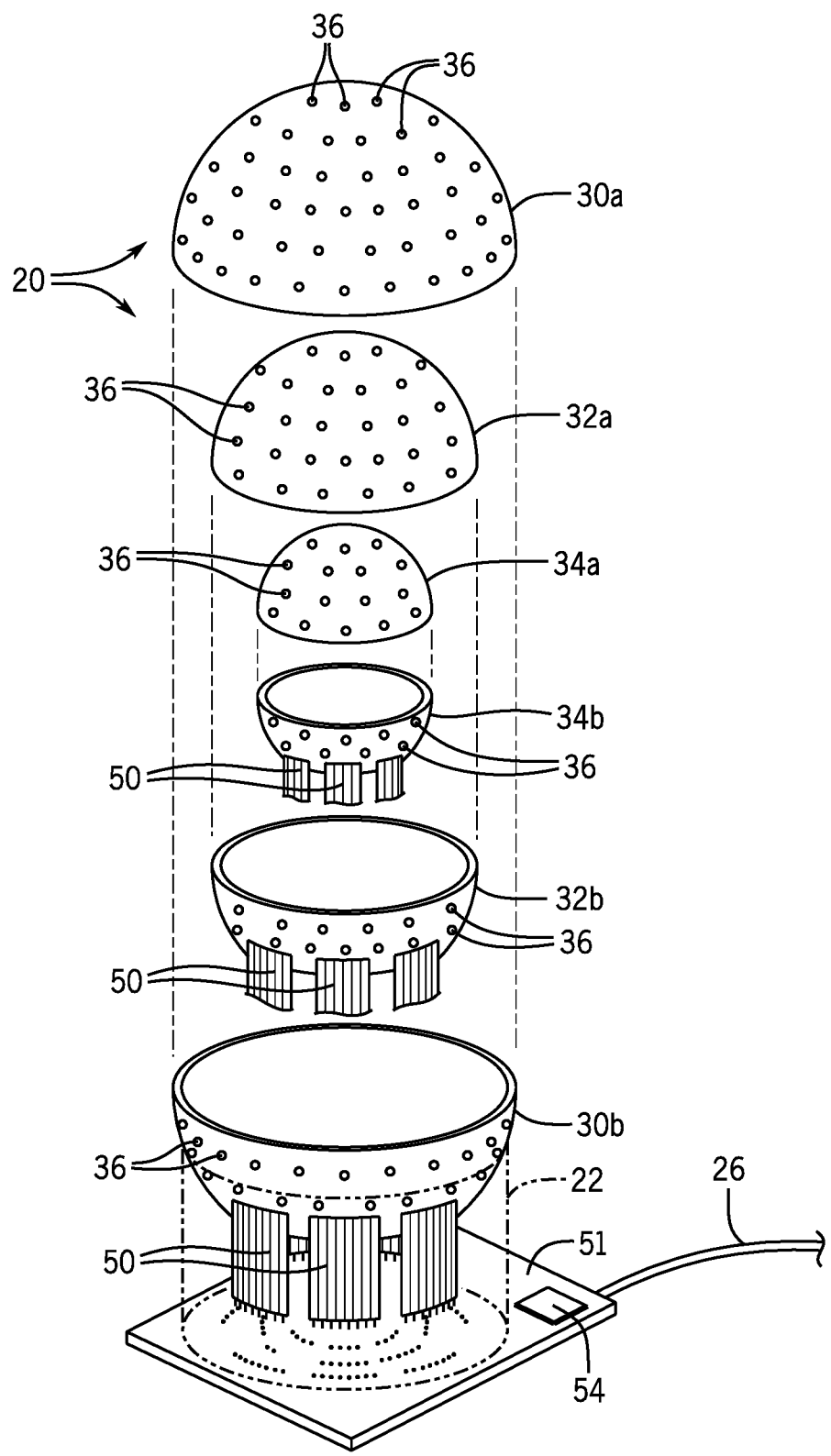
FIG. 2 is an exploded perspective view of the dose verification instrument of FIG. 1 showing an assembly method and routing of electrical conductors.

Referring now also to FIG. 2, a volume 20 having a spherical volume may be constructed of a set of nesting hemi-spherical shells. The shells may include a first pair of outer hemispherical shells 30a and 30b that may be assembled to provide a spherical volume enclosing a second set of lesser-diametered inner hemispherical shells 32a and 32b, which in turn may be assembled to enclose a smaller spherical volume receiving a pair of shell hemispheres 34a and 34b. The shell hemispheres 34a and 34b are solid and thus complete an assembly of a solid volume 20. The volume 20 may be on the order of 4000 cm$^3$ and in some embodiments greater than 2000 cm$^3$ or greater than 1000 cm$^3$ While only two inner hemispherical shells 32 are shown for simplicity, one embodiment of the invention contemplates sixteen such nesting shells (one pair of outer shells 30, fourteen pairs of inner shells 32, and one central pair of shell hemispheres 34). In this embodiment, the largest outer shell 30 may have an outer diameter of 22 cm and the outer diameter of each succeeding shell may be reduced successively by approximately 1 cm to enclose a central solid sphere formed of shell hemispheres 34a and 34b having a 2 cm radius.

The material of the shells 30, 32 and shell hemispheres 34 may be a water equivalent material, for example, polystyrene or PMMA (polymethyl methyl acrylate) or other similar materials mimicking watery tissue. Water equivalent material is material that provides similar attenuation and scattering to water, for example, conforming in these measurements with water by plus or minus 10%. Generally, the shells 30 and 32 may fit closely together so that the interior volume of the measurement volume 20 is at least 90% and preferably greater than 95% water equivalent material to the exclusion of air.

Figure 4:
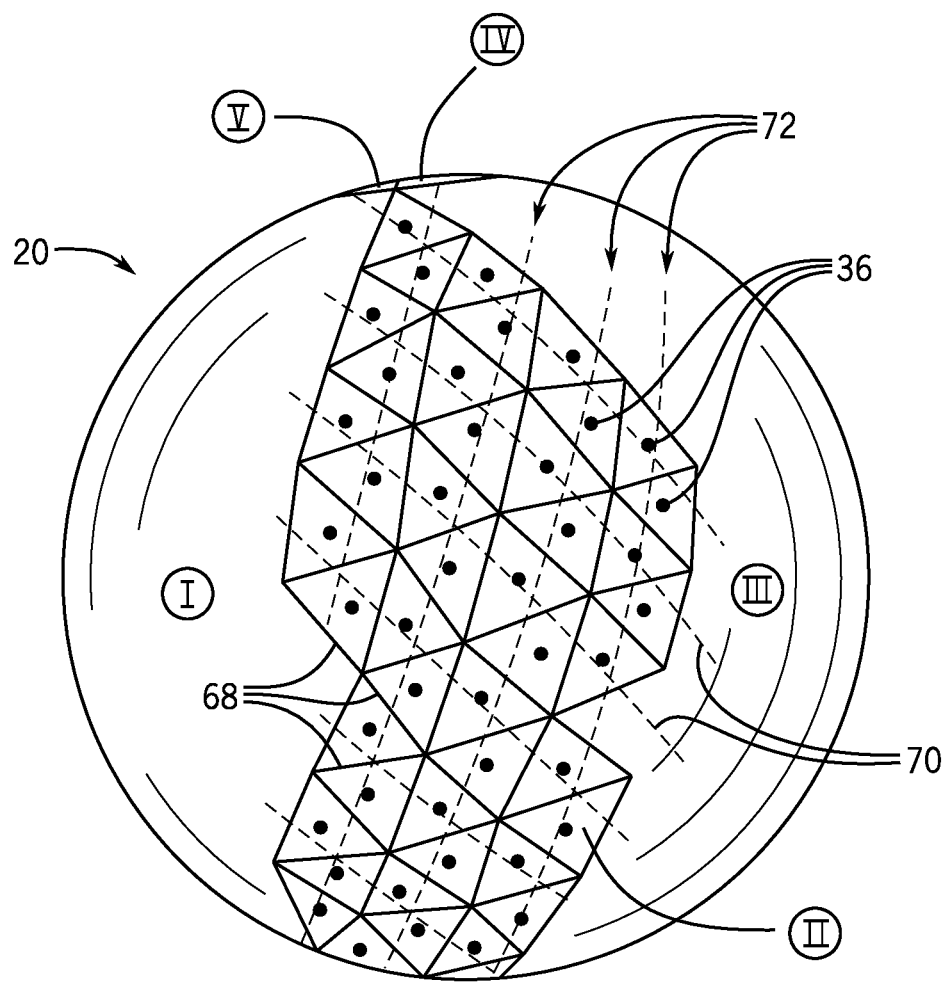
FIG. 4 is an elevational perspective view of an outside of the detector of FIG. 1 showing regular spacing of detector elements and readout circuitry on the instrument according to a geodesic overlay.

Referring also to FIG. 4, affixed to the outer surface of each of the shells 30-34 is a set of solid-state radiation detectors 36, for example, solid-state diodes, distributed uniformly or isotropically over those outer surfaces. One method of distributing the solid-state electronic radiation detectors 36 is by placing them in centers of equilateral triangles formed by a geodesic polyhedron conforming to the surfaces of the volume 20. The detectors 36 may make use of any known solid-state radiation detection technology including those based on silicon, graphene, copper and the like.

The radiation detectors 36 are distributed over the entire outer surfaces of the shells 30, 32, or 34 so that trajectories through the volume 20 will intersect detectors 36 that are spaced from each other along the surface on opposite sides of each of the shells 30, 32 or 34.

In one embodiment, the outermost shell 30, when 22 inches in diameter, will have over 5000 detectors 36, and the combined number of detectors 36 in all of the shells 30, 32, or 34 in a sixteen-shell embodiment will exceed 20,000. The invention contemplates that the number of detectors 36 in the outermost shell 30 will exceed 100 and desirably be more than a thousand.

The detectors 36 of each shell 30, 32 and 34 together define a closed surface 40 that has surface normals 42 distributed at multiple angles lying in each of a pair of vertical and mutually perpendicular planes 44. While the invention contemplates the possible use of spherical diodes, when planar diodes are used, the sensitivity of the diode depends on the angle of received radiation with respect to a planar face of the diode defined by these surface normals. Desirably at least ten different angles will be represented in each plane 44. Desirably the surface normals at each detector 36 may be spaced approximately evenly over 360° within each plane 44. For example, the angles between each detector 36 may vary by less than 50% and in some embodiments less than 25% from the average angular spacing between each detector 36. In this way, radiation received at a wide range of angles in both azimuth and altitude, corresponding to modern radiation therapy machines, can be accurately and consistently assessed. Generally, the spacing between detectors will be also be approximately uniform and the distance between any two detectors will vary by less than 50% and in some embodiments less than 20% from the average detector-to-detector spacing.

Figure 3:
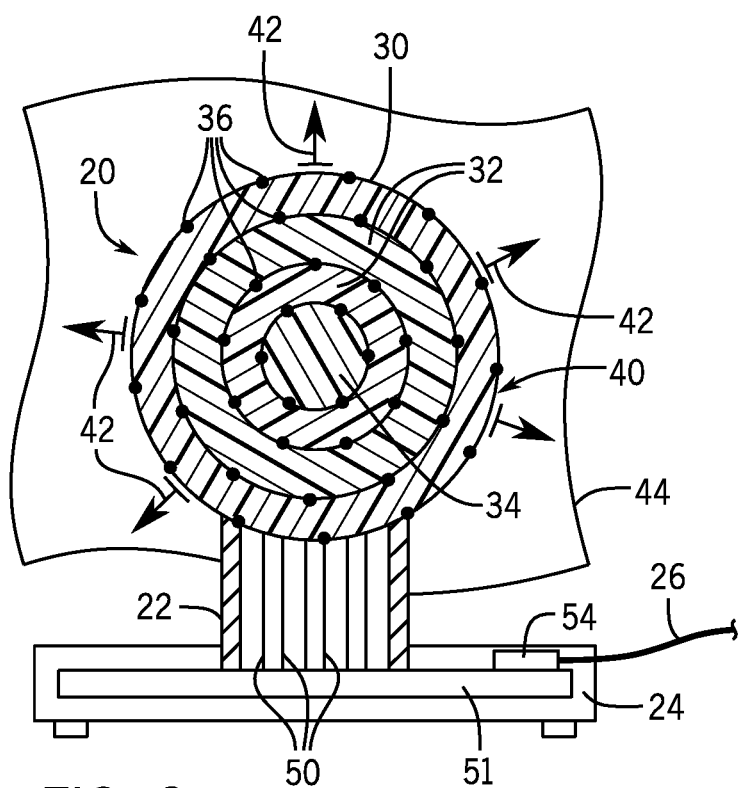
FIG. 3 is an elevational cross-sectional view through the assembled instrument of FIG. 2 showing surface normals of the detectors such as reduce detector error from oblique beams.

Referring still to FIGS. 2 and 3, each of the detectors 36 may provide electrical signals indicating an integrated dose at the detector 36 as modified by the water equivalent material of the volume 20. These signals, as will be discussed in more detail below, may be conducted along thin copper conductors, for example, having a diameter of approximately 200 μm passing through the volume 20. These thin conductors are collected together in ribbon cables 50 passing outward and downward from the respective lower shells 30b, 32b, and 34b around a lower longitudinal circumference of the outer surfaces of the lower shells 30b, 32b and hemisphere 34b. Shells 30b or 32b outside of a given shell 32 or 34 will provide for narrow slots through which the ribbon cables 50 may pass so that they may all descend downward concentrically inside the column 22 to connect at a printed circuit board 51 providing traces leading to an interface circuit 54.

Desirably the column 22 is also constructed of water mimicking material or preferably a material providing less absorption and scattering than water. The column 22 may include cutouts to reduce its effect on the radiation passing through the volume 20 and the material of the ribbon cable may likewise be adapted to minimize disruption from the x-rays. The downward exiting of the copper conductors minimizes scatter from the conductors that would affect the detectors 36 for common angles of radiation beams 14, that is, except for a range of angles that are nearly vertically upward.

Signals from each detector 36 may be collected and digitized by the interface circuit 54 to send along the electrical cable 26 to the computer 28 (shown in FIG. 1). Likewise, active matrix strobe signals can be sent from the interface circuit 54 to activate particular detectors 36 as will be discussed.

Figure 5:
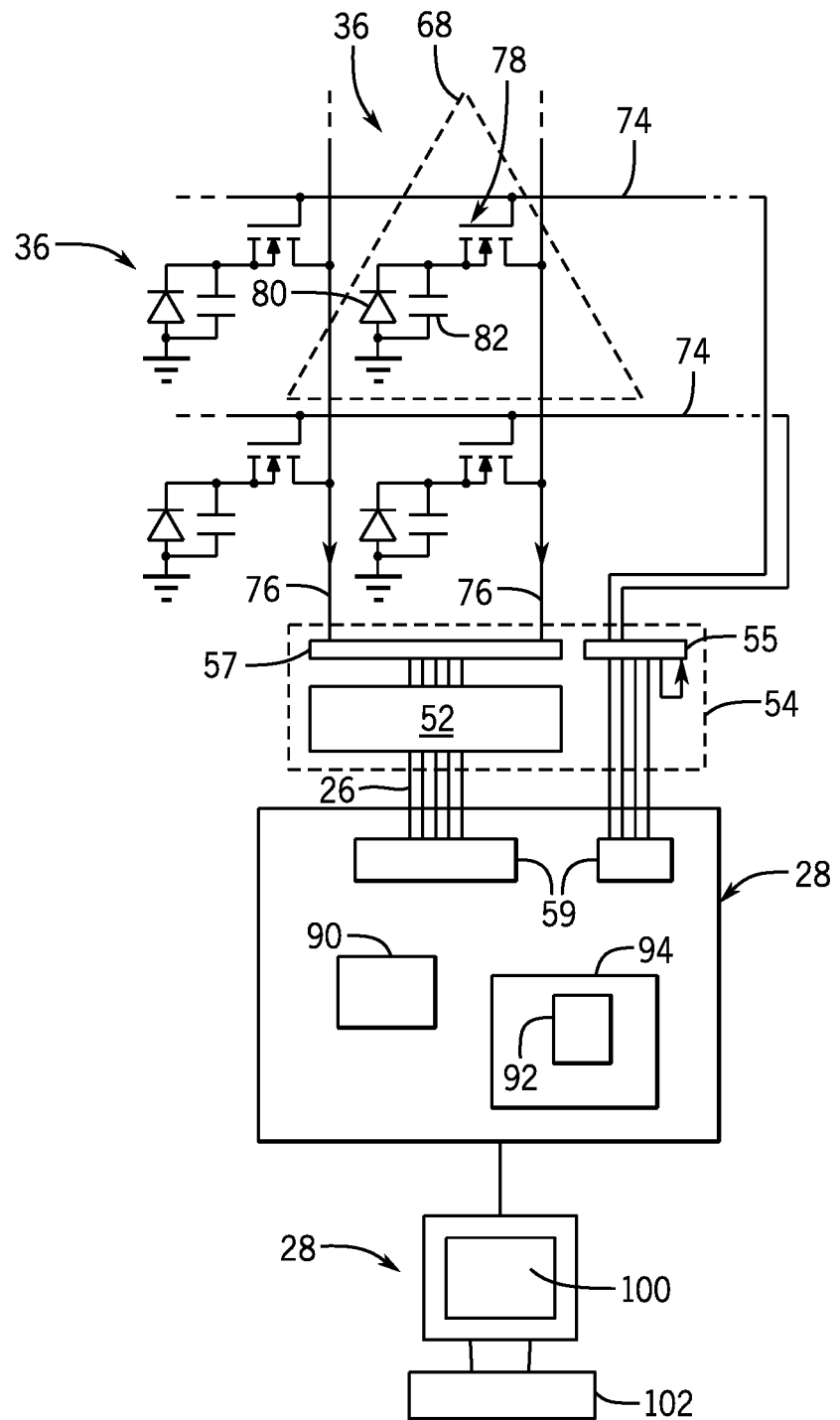
FIG. 5 is a schematic block diagram showing the electrical components associated with the detector and readout circuitry.
Figure 6:
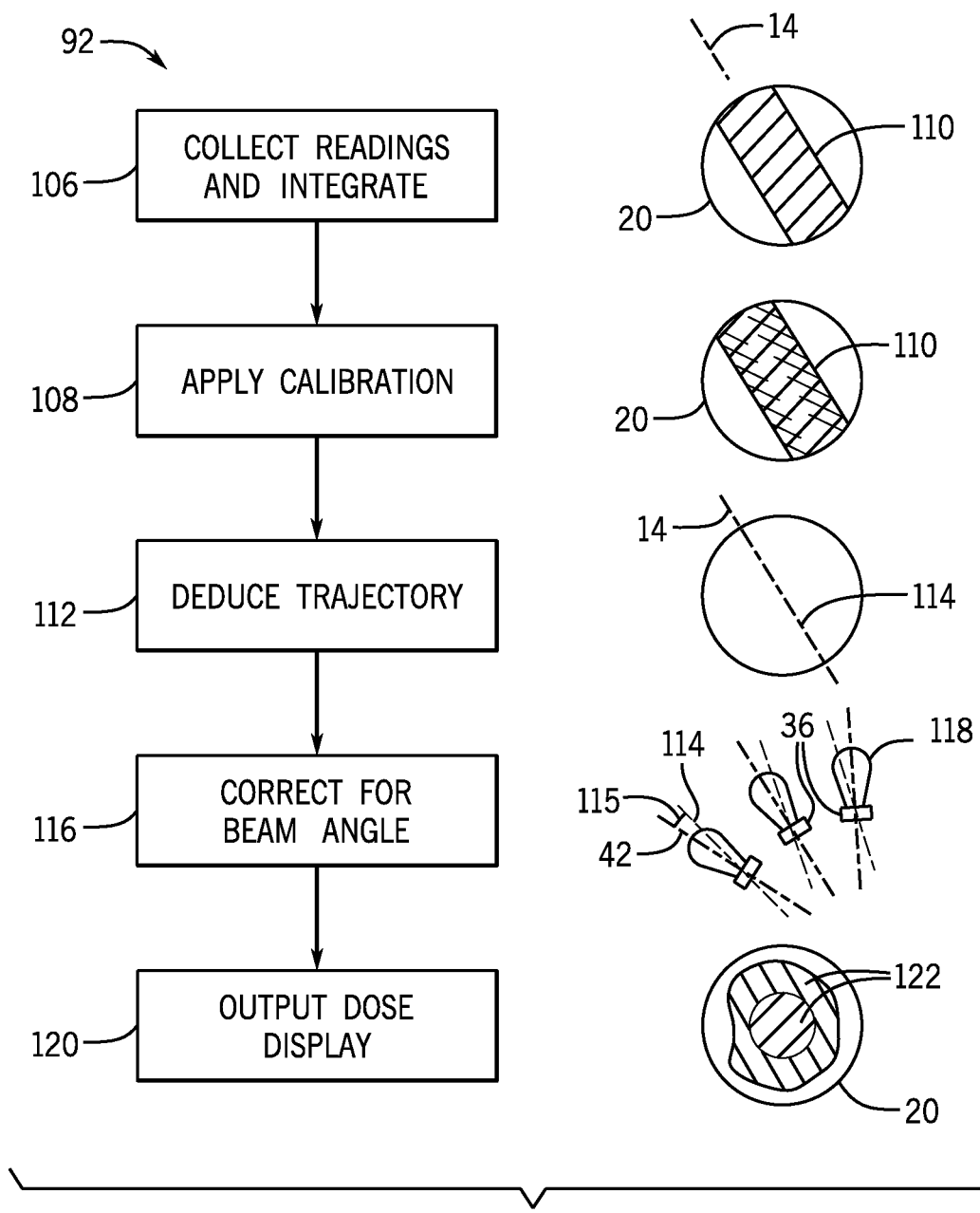
FIG. 6 is a flowchart and diagrammatic representation of data processing employed by an electronic computer that may be associated with the detector of the present invention.

Referring now to FIGS. 5 and 6, each of the solid-state detectors 36 may be positioned, for example, at a center of an equilateral triangle of a set of triangles that tessellate over the surface of the respective shells 30, 32 and 34 and which form a geodesic polyhedron discussed above. These triangles 68 may be divided, for example, into sets of triangles forming one of five sectors (I-V) being swathes of a sphere extending generally longitudinally as depicted in FIG. 6.

Within each sector (I-V) the triangle 68 are aligned to roughly approximate regular rows 70 and columns 72 suitable for efficient multiplexing. Generally the rows 70 and columns 72 will not be uniform for a given sector. For each sector I-V, strobe lines 74 may interconnect the detectors 36 of each triangle 68 of the given row 70, and output lines 76 may interconnect the detectors 36 of each triangle 68 of the given column 72 to provide for active matrix multiplexing. For each sector I-V, the strobe lines 74 and output lines 76 are connected together into the ribbon cable 50 shown in FIG. 3 for separate readout. A given sector I-V can include from 27 to 972 detectors depending on the layer's diameter. The separation between detectors will typically be less than 10 mm and preferably less than 7 mm and typically approximately 5.5 mm.

Referring specifically to FIG. 5, in each triangle 68, strobe lines 74 may connect to the gate of a thin film transistor 78. The transistor 78 may connect an output line 76 for the detector 36 of the triangle 68 to the anode of a diode 80 that provides for the radiation sensitivity. The cathode of the diode 80 may be connected to a ground wire (not shown) that passes in a raster fashion through each triangle 68 of the rows 70 and columns 72. A capacitor 82 may shunt the anode and cathode of the diode 80 and provides for the integrating action of the detector 36. The diodes 80 may each have an area of approximately 0.5×0.5 in a plane of the detector 36 and a thickness of approximately 0.3 mm along the surface normal.

To interrogate the dose received by the diode 80 at a given triangle 68 (time integrated in the capacitor 82), the corresponding strobe line 74 is raised by the output of the first multiplexer 55 of the interface circuit 54 (multiplexed among the strobe lines 74). An output line 76 from the detector 36 of the triangle 68 is read by a second multiplexer 57 and provided to analog-to-digital converter 52 and received by electrical cable 26 to be sent the computer 28. This process may be repeated for each of sectors I-V, for example, by parallel similar circuits.

Data is received at the computer 28 through interface circuits 59 and processed by one or more processors 90 executing a stored program 92 in a computer memory 94 to provide output data on an associated terminal screen 100, for example, selected by the user through a keyboard 102.

Referring now to FIG. 7, the program 92, at process block 106, controls the interface circuit 54 to collect dose data from each detector 36 on a regular time basis to provide for consistent dose integration. Generally, this collection process will provide a dose swath 110 of excited detectors 36 indicating a path of a radiation beam 14 through the volume 20. The irregular number of rows and columns in each sector can be accommodated through a mapping table that maps particular row and column addresses to geometric locations on or in the volume 20. The signals at this point may be subject to filtering such as low-pass filtering to remove noise components.

At process block 108 a calibration factor may be applied to the readings from each detector 36 empirically determined at the time of manufacture to correct for variations in dose sensitivity of each diode 80. After application of these calibration factors, the data will reveal dose variations within the swath 110.

At process block 112 the trajectory 114 of the radiation beam 14 may be determined by geometric analysis to produce a trajectory difference 115 being an angular difference between the trajectory 114 at each detector 36 and its surface normal 42. The geometric analysis can take into account the variations in dose as corrected by process block 108, for example, to provide weighted centroids that better reflect the center of the radiation beam. This trajectory difference 115 may be applied at process block 116 against a known angular sensitivity curve 118 of the diode 80 to determine apparent reductions in dose based on the obliqueness of the trajectory 114 with respect to the surface normal 42 of the detector 36. In this way apparent dose falloff based on the obliqueness of the angle may be accommodated for a wide range of radiation angles.

At process block 120 this corrected dose information may be used to provide, for example, 3D volumetric dose maps 122 of the dose within the volume 20. Because of the nature of the water mimicking material in the volume 20, this dose accurately characterizes scattering and diffusion of radiation that would be experienced in human tissue.

The data collected by the present invention may be used to provide a variety of output displays directly including, for example, a conformity index (CI) described generally in Shaw E, et al. Radiation therapy oncology group: Radiosurgery quality assurance guidelines. Int. J. Radiation Oncology Biol. Phys. 27, 1231-1239 (1993). Alternatively the invention can provide a gradient index (GIA) described at Feuvret L, et al. Conformity index: A review. Int. J. Radiation Oncology Biol. Phys. 64, 2, 333-342 (2006) or a dose volume histogram (DBH) as discussed in Drzymala R E, et al. Dose-volume histograms. Int. J. Radiation Oncology Biol. Phys. 21, 71-78 (1991) or a percent dose difference per distance to agreement (% Diff/DTA) discussed in Low D A, et al. A technique for the quantitative evaluation of dose distributions. Med. Phys. 25, 5, 656-661 (1998). Each of these above references is hereby incorporated into entirety by reference.

It will be appreciated that the structures of the volume 20 and column 22 described above may be produced by injection molding or by 3D printing or other fabrication techniques and that the copper conductors may be laid and glued by hand or may be printed using conductive printed inks on a semiautomatic basis. In some embodiments, the shells 30, 32, and 34 may be fabricated separately and wired and then glued together with conductors interconnected by connectors, conductive adhesive tape, soldering or the like.

The term closed surface is intended to describe the surface that encloses a volume, for example, such as would hold water if fashioned of water impermeable material. The invention contemplates that the volume 20 may be of a variety of convex shapes including spheres, ovoids and the like but need not be symmetric. The diameter of the volume 20 is intended to be large enough to subtend the treatment area of tumors and yet to provide treatment of tumors smaller than 7 mm in diameter (less than 0.18 cm$^3$) and to provide dose resolution for target volumes of 0.01 to 10 cm$^3$. Accordingly a range of diameters of the volume 20 is contemplated from 2-40 cm. It will be appreciated that the outer close surface defined by the outermost photosensitive detectors need not be an exposed surface but can be coated or protected by additional material of low radiation attenuation and scattering.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A radiotherapy dose verification instrument comprising:
   a radiolucent support structure;
   a plurality of first solid-state electronic radiation detectors held by the radiolucent support structure at separated locations defining an outer closed surface enclosing a volume of the radiolucent support structure;
   a plurality of second solid-state electronic radiation detectors dispersed within the volume; and
   a set of conductors communicating with each of the first and second plurality of solid-state electronic radiation detectors to receive electronic signals from corresponding solid-state electronic radiation detectors indicating radiation dose at each of the first and second plurality of solid-state electronic radiation detectors for output;
   wherein the outer closed surface presents surface normals at the solid-state electronic radiation detectors distributed at multiple angles in each of two perpendicular planes.

2. The radiotherapy dose verification instrument of claim 1 wherein more than 90% of the volume is occupied by a water equivalent material.

3. The radiotherapy dose verification instrument of claim 1 wherein the first plurality of solid-state electronic radiation detectors is substantially uniformly distributed over the outer closed surface.

4. The radiotherapy dose verification instrument of claim 1 wherein the second plurality of solid-state electronic radiation detectors is substantially uniformly distributed within the volume.

5. The radiotherapy dose verification instrument of claim 1 wherein the second plurality of solid-state electronic radiation detectors defines a set of corresponding nested closed surfaces concentric within the outer closed surface and wherein the second plurality of solid-state electronic radiation detectors is substantially uniformly distributed over corresponding nested closed surfaces.

6. The radiotherapy dose verification instrument of claim 5 wherein the volume comprises a set of inter-fitting shells each having an outer surface defining at least one of the outer closed surface or corresponding nested closed surface, the inter-fitting shells adapted to be individually fabricated.

7. The radiotherapy dose verification instrument of claim 1 wherein the first plurality of solid-state electronic radiation detectors is positioned to measure the entrance and exit doses of radiation passing along a straight line through the volume.

8. The radiotherapy dose verification instrument of claim 1 wherein the radiation detectors are integrating detectors of radiation intensity.

9. The radiotherapy dose verification instrument of claim 1 wherein a total number of the plurality of solid-state electronic radiation detectors is in excess of 20,000.

10. The radiotherapy dose verification instrument of claim 1 wherein a volume is greater than 500 cm$^3$.

11. The radiotherapy dose verification instrument of claim 1 wherein average separation of the plurality of solid-state electronic radiation detectors is less than 7 mm.

12. The radiotherapy dose verification instrument of claim 1 wherein including a calibration circuit receiving the electronic signals and operating to:
 (1) determine trajectory of a radiation beam striking the radiolucent support structure and only a subset of the plurality of solid-state electronic radiation detectors; and
 (2) correct electronic signals for angular sensitivity variations of the subset of the plurality of solid-state electronic radiation detectors based on the deduced trajectory.

13. The radiotherapy dose verification instrument of claim 1 wherein the outer closed surface is a sphere.

14. The radiotherapy dose verification instrument of claim 1 further including an electronic computer executing a stored program held in non-transitory memory and operating to receive the electronic signals to provide an output selected from the group consisting of a conformity index, a gradient index, a dose volume histogram, and a 3D percent dose difference per distance to agreement.

15. The radiotherapy dose verification instrument of claim 1 wherein the first plurality of solid-state electronic radiation detectors are connected by logical row and column conductors and wherein each of the solid-state radiation detectors provides a transistor and a storage element, the transistor being activated by one of the row and column conductors to communicate between and other of the row and column conductors electrical charge on the storage element.

16. The radiotherapy dose verification instrument of claim 15 wherein the storage element receives charge from a diode radiation detector associated with each of the solid-state radiation detectors.

17. The radiotherapy dose verification instrument of claim 15 wherein the logical rows and conductors provide for unequal numbers of solid-state electronic radiation detectors along the rows and columns to define spherical lanes.

* * * * *